United States Patent
Cashaw et al.

[11] Patent Number: 5,843,267
[45] Date of Patent: Dec. 1, 1998

[54] SANITARY NAPKIN WITH SOFT, PLIABLE SIDES AND RELATIVELY STIFF ENDS

[75] Inventors: Alan G. Cashaw, Brick; Tong-Ho Hsieh, Marlboro; Thomas J. Luceri, Neshanic Station, all of N.J.; H. Michael Moscherosch, Neuss, Germany; Subramanian Srinivasan, East Brunswick, N.J.

[73] Assignee: McNeil-PPC, Inc.

[21] Appl. No.: 667,535

[22] Filed: Jun. 21, 1996

Related U.S. Application Data

[60] Provisional application No. 60/000,732 Jun. 30, 1995.
[51] Int. Cl.$^6$ ....................................................... A61F 13/15
[52] U.S. Cl. ............................................. 156/324; 604/387
[58] Field of Search ................................. 156/324, 292, 156/267, 269; 604/387, 374

[56] References Cited

U.S. PATENT DOCUMENTS

| | | | |
|---|---|---|---|
| 3,570,491 | 3/1971 | Sneider | 604/387 |
| 4,259,958 | 4/1981 | Goodbar | 604/374 |
| 4,518,451 | 5/1985 | Luceri et al. | 156/260 |
| 4,654,040 | 3/1987 | Luceri | 156/202 |
| 4,900,377 | 2/1990 | Redford | 156/267 |
| 5,674,341 | 10/1997 | Ng | 156/230 |

FOREIGN PATENT DOCUMENTS

| | | |
|---|---|---|
| 0 176 853 A1 | 4/1986 | European Pat. Off. . |
| 0 359 501 | 3/1990 | European Pat. Off. . |
| 0 508 485 A1 | 10/1992 | European Pat. Off. . |
| 0 471 114 A2 | 12/1992 | European Pat. Off. . |
| 0 572 033 A2 | 12/1993 | European Pat. Off. . |
| 2.209.520 | 7/1994 | France . |
| WO 91/18573 | 12/1991 | WIPO . |
| WO 93/09744 | 5/1993 | WIPO . |

*Primary Examiner*—Daniel Stemmer

[57] ABSTRACT

A disposable absorbent article or pad provides improved wearer comfort because it is shaped to provide an optimal fit to the user's undergarment, it has soft, flexible sides to prevent chafing of the user's thighs, and it has relatively stiff ends to prevent the ends from curling up during use. The difference in flexibility between the pad's ends and sides is achieved by placing a core of absorbent material end to end along the longitudinal axis of the product and centered in the midsection of the product so that the absorbent material is present in the peripheral sections of the product's ends but is absent in the peripheral sections of the product's sides.

11 Claims, 3 Drawing Sheets

SANITARY NAPKIN WITH SOFT, PLIABLE SIDES AND RELATIVELY STIFF ENDS

CROSS-REFERENCE TO RELATED APPLICATIONS

The present application claims priority of the provisional application, Ser. No. 60/000,732, filed Jun. 30, 1995, the disclosure of which is hereby incorporated by reference.

BACKGROUND OF THE INVENTION

The present invention relates to an absorbent article particularly suited for everyday feminine hygiene and for protecting an undergarment against staining from light, daily secretions and discharges. It comprises a very is thin, lightweight, highly absorbent pad which is soft, supple and easily conformable to the body and the garment to which it is adhesively attached.

The prior art is replete with patents relating to protective pads and shields since the protection of undergarments from staining, especially for many women who are troubled with frequent, light bodily discharges, has been a long standing problem. These patents generally describe layered structures having a porous body contacting cover layer, a liquid impermeable garment side barrier layer, and a core of absorbent material between the body contacting layer and the barrier layer. An adhesive is attached to the garment side of the fluid barrier to secure the assembled shield to the crotch portion of an undergarment. A release layer is removably affixed to the adhesive layer to keep the adhesive from contacting anything until it is placed in the undergarment. The components described above are typically combined in either an overwrap or die-cut product design.

In the overwrap design, the porous body contacting cover layer is wrapped around the absorbent material and this composite is then attached to the liquid impermeable barrier layer. While this overwrap design provides soft, rounded edges for the product, it does have a significant limitation in that it yields a rectangular shaped product, i.e. a product with parallel sides. A rectangular product shape provides suboptimal coverage of the hourglass shaped panty crotch to which it is applied.

To provide improved coverage, a disposable sanitary napkin may match the hourglass shaped panty crotch. A die-cut product design may be used to achieve this hourglass or any other shape. In the die-cut design, the porous body contacting cover layer, the absorbent material, and the impermeable barrier layer are laminated together and die-cut into an hourglass or other shape. A peripheral seal is typically used to ensure that the product does not come apart during use. In the prior art, there are numerous examples of die-cut products in which the cover and absorbent and barrier are all present in the entire peripheral edge of the product (e.g. CAREFREE® Comfort, currently sold by Johnson & Johnson GmbH). There are also numerous examples of die-cut products in which only the cover and barrier are present in the entire peripheral edge of the product (e.g. ALWAYS ALLDAYS Normal, currently sold by Procter & Gamble in Europe). Another example of this construction can be found in Kimberly-Clark, EP-A-0 471 114. However, both of these types of constructions have problems associated with them.

For die-cut products in which the cover and absorbent and barrier are all present in the entire peripheral edge of the product, the process of sealing the peripheral edge causes the edge to become relatively stiff, especially if there is some quantity of absorbent material in the product. The stiff peripheral edge resists bending and therefore, the product's side edges can chafe and otherwise irritate a user's thighs when worn. To increase the absorbent capacity in die-cut products, the amount, and hence the thickness, of the absorbent material is generally increased. Because the increased absorbent thickness would extend to the peripheral edge, the seal would become even thicker and more uncomfortable. Thus, there are limitations in absorbent capacity of these products.

To prevent the problem of irritation from the pad's stiff side edges, some die-cut products have only the cover and barrier present in the peripheral edge of the product and the entire absorbent core and possibly other components are located inward of the peripheral seal. However, while soft, pliable edges are preferred for the sides of the product, they are not desirable for the pad ends. This is because the soft, pliable edges at the product's ends can easily curl up in use and expose the product's positioning adhesive to the user's skin, thereby causing user discomfort. The more rigid the product's ends, the less likely that they will curl up in use and create wearing discomfort. A further disadvantage of die-cut products in which the entire absorbent core is located inboard of the perimeter seal is that the absorbent core must be cut or formed separately and then carefully placed into the product such that it does not extend into the perimeter seal. This type of "cut and place" process is slower than a continuous process and frequently leads to a higher rate of process waste because of reject products in which the absorbent core is not aligned correctly.

Therefore, it is an object of this invention to provide the user with a sanitary napkin which is shaped to provide optimal panty coverage, has soft, pliable side edges to prevent chafing of the user's thighs, and has relatively stiff ends to prevent the ends from curling up during use. A further object of this invention is to provide such a sanitary napkin which may be made by a continuous process.

SUMMARY OF THE INVENTION

The disposable absorbent article of the present invention comprises a thin, highly absorbent pad having a porous body-side cover, an absorbent insert, and a liquid impermeable or repellent barrier. Optionally, the product may include a positioning means for attaching the pad to an undergarment, and a release layer to protect the positioning means prior to use. The absorbent insert is located between the cover and barrier and about the pad's longitudinal axis. The absorbent insert has a maximum width which is less than the maximum width of the pad.

Thus, the insert does not extend fully to the lateral sides of the pad. The cover and barrier may be present about the entire periphery of the pad. The result is a product with pad edges having differential stiffness; specifically, the pad ends are stiffer than the pad sides.

BRIEF DESCRIPTION OF THE DRAWINGS

In the accompanying diagrammatic drawings which illustrate the invention.

DETAILED DESCRIPTION OF THE INVENTION

Figure 1A:
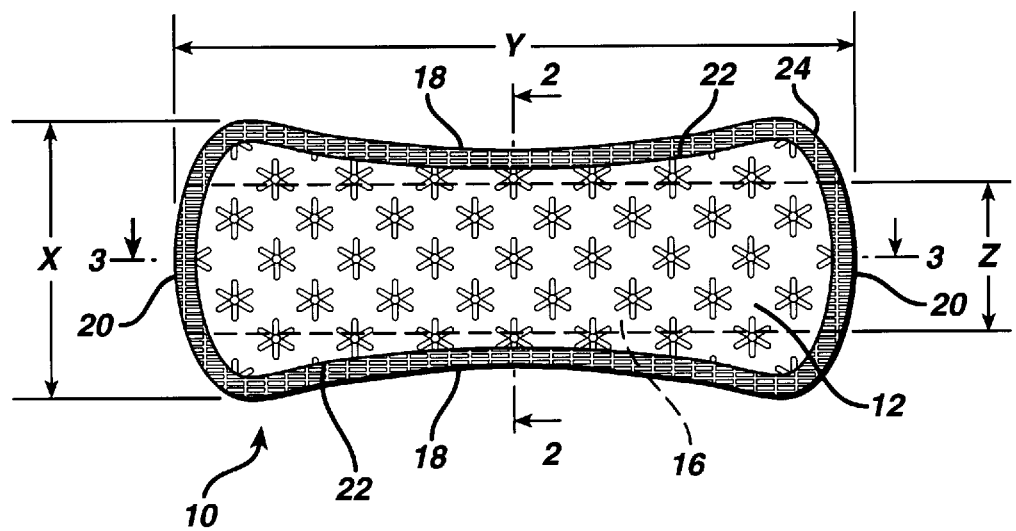
FIG. 1A is a top plan view of one embodiment of a disposable sanitary napkin of the present invention.
Figure 1B:
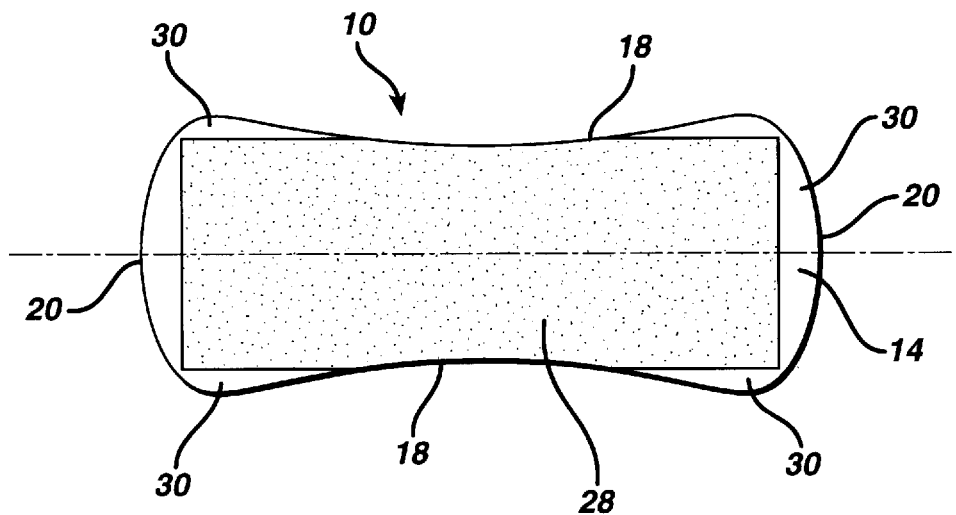
FIG. 1B is a bottom plan view of one embodiment of a disposable sanitary napkin of the present invention.

As seen in FIGS. 1A and 1B, a preferred embodiment of the pad 10 is a die-cut product having an hourglass shape.

The product is about 6.1" long. It has a minimum width of 2" proximate the midpoint of the pad and a maximum width of about 2.6" proximate the longitudinal ends of the pad. The product has a porous, body-side cover 12, a liquid-impervious barrier layer 14, and an absorbent layer 16 therebetween. The article has a maximum width dimension X, a length dimension Y, lateral sides 18, and longitudinal ends 20. Preferably, both the body-side cover 12 and the barrier layer 14 extend to the peripheral edges extending along the lateral sides 18 and longitudinal ends 20 of the pad 10. In contrast, the absorbent layer 16 has a maximum width Z which is less than the maximum width X of the pad 10. Therefore, the absorbent layer 16 does not extend fully to the lateral side edges 18 of the product. However, the absorbent layer 16 does extend to the longitudinal ends 20 of the pad.

Because the absorbent layer 16 does not extend fully to the lateral sides 18 of the pad 10, the side portions 22 where the absorbent layer 16 is not present have less laminated material and are less stiff. On the other hand, the absorbent layer 16 extends to the longitudinal ends 20 of the pad, and therefore, these ends are stiffer than the lateral sides 18. This construction allows the use of a continuous absorbent layer 16 in the manufacture of the pad 10 as described below with its increased efficiency and reduced process waste. In addition, the construction also provides softer sides 18 to reduce potential chafing for the user while allowing stiffer ends 20 to prevent curling of the product ends during use.

The body-side cover 12 may comprise any known porous material with a suitable body contacting surface including, but not limited to nonwoven webs, apertured films, plastic nets, and the like. In the preferred embodiment, the cover 12 is made of a fibrous nonwoven composite of bicomponent fibers and pulp fluff. The body-side cover may be embossed, e.g., with a floral or other decorative pattern, as illustrated in FIG. 1A.

Bicomponent fibers are known in the art and are composed of two polymers with different melting points. At least a portion of the outer surface of each bicomponent fiber comprises the lower melting polymer. The two polymers may be arranged such that a cross-section of the fiber shows the two polymers in a side-by-side array. Alternatively, the polymers may be positioned in a so-called sheath/core arrangement, in which a core of higher melting polymer is surrounded by a sheath of lower melting polymer. A preferred bicomponent fiber is BASF "BICO" code 1050 fiber, a 3.0 denier, 1.5" long staple fiber made of a polyester core and a high density polyethylene sheath (BASF Corporation, Charlotte, N.C.). Similar fibers (polyethylene sheath and polypropylene core) are available as Danaklon ES-C or ES Bico (Danaklon A/S, Varde Denmark). Pulp fibers may be obtained as IP "SUPERSOFT" ELM supplied by the International Paper Company (Memphis, Tenn.), "RAYFLOC" XJ-HM E-Type Cellulosic Fluff Pulp, (ITT Rayonier), or Korsnäs Vigorfluf-EN White (Korsnäs, Gavle, Finland).

In the preferred embodiment of the cover layer 12, a blend of pulp and bicomponent fibers is formed into a relatively high bulk, low density nonwoven web as described in Mays et al., EP 070 164, which is herein incorporated by reference. The material has a basis weight of 2.5 oz/yd$^2$ and an overall fiber composition of about 46% bicomponent fiber/54% pulp. The material has a screen side veneer of a 0.32 oz/yd$^2$ nonwoven web formed of 3 denier BASF "BICO" 1050 fibers, an absorbent layer of a 1.87 oz/yd$^2$ mixture of about 75 wt-% "RAYFLOC" XJ-HM pulp and about 25 wt-% 3 denier BASF "BICO" 1050 fibers, and a second veneer of a 0.32 oz/yd$^2$ nonwoven web formed of 3 denier BASF "BICO" 1050 fibers. The two veneers substantially sandwich the BICO/pulp layer. The screen side of the body-side cover 12 material is preferably oriented toward the body in the laminated product. The material may also be formed of top and bottom veneers of 2 denier Danaklon ES-C or ES Bico fibers and an absorbent layer of 23 wt-% 3 denier Danaklon fibers and 77 wt-% pulp (Korsnäs or ITT Rayonier).

Figure 2A:
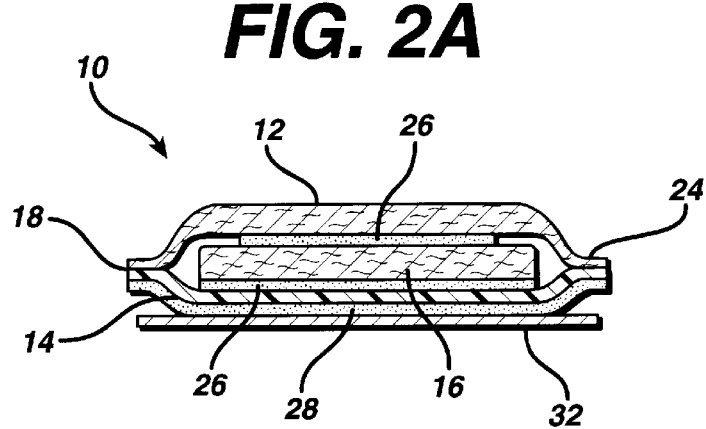
FIG. 2A is an enlarged section taken along line 2—2 of FIG. 1A.
Figure 2B:
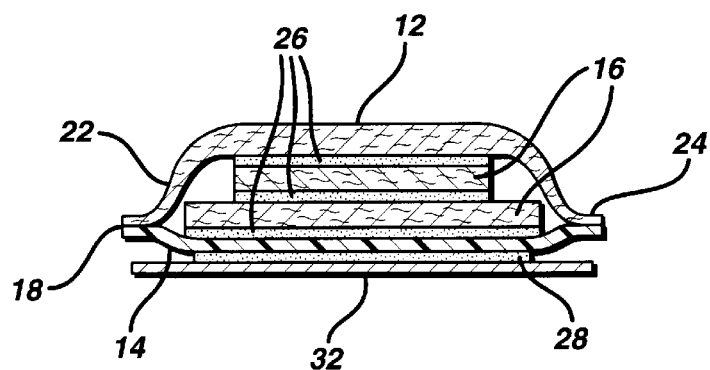
FIG. 2B is an enlarged section taken of an alternative embodiment along line 2—2 of FIG. 1A.
Figure 3:
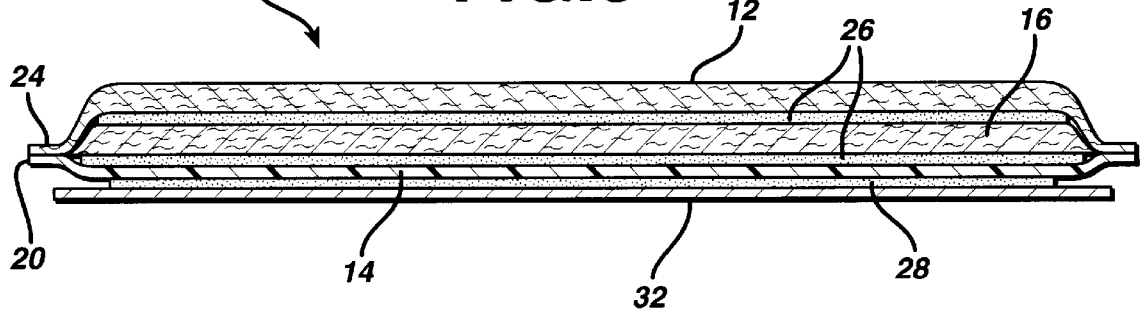
FIG. 3 is an enlarged section taken along line 3—3 of FIG. 1A.

The absorbent layer 16 is located adjacent to the cover layer 12. The absorbent layer 16 has a length Y which is substantially the same as the length Y of the cover 12 and barrier layers 14 and a maximum width Z which is less than the maximum width X of the pad 10. Therefore, while the absorbent layer 16 extends to the longitudinal pad ends 20, it does not extend fully to the lateral sides 18. Additional absorbent material is located along the longitudinal center of the product where it is needed, and it is located away from those portions 22 of the lateral edges 18 which may cause problems in use. Preferably, the absorbent layer 16 is not captured by the peripheral seal 24 along the pad sides 18 and is captured by the peripheral seal 24 at both ends 20 of the pad 10. The absorbent layer 16 may comprise any material which absorbs bodily secretions including, but not limited to pulp, polymeric fibers and filaments, sphagnum moss, natural fibers, superabsorbent polymers (including fibers, particulate material and foams), absorbent foams, and other such absorbent materials. The absorbent layer 16 may also include additional materials such as odor control means for controlling undesirable odors, indicator means for indicating wetness, means for delivering medicaments such as encapsulated medicaments, and means for maintaining skin moisture such as encapsulated moisturizers. Odor control means may be used to sequester or react with (e.g., neutralize) odor-causing compounds, mask odors, absorb or adsorb odor-causing compounds, prevent odor causing agents from forming, or operate through similar mechanisms. Representative, non-limiting examples of odor control means include ethylene diamine tetraacetate (EDTA), zeolites, baking soda (sodium bicarbonate), activated charcoal, fragrances, and the like. The absorbent layer 16 may comprise one or more layers in an overlapping or side-by-side arrangement. See for example, FIG. 2B which is an alternative view along line 2—2 of FIG. 1A. These multiple absorbent layer layers may be of similar width and thickness or varying dimensions. In the preferred embodiment, the absorbent layer is a 1.5" wide layer of the same material (oriented with screen side toward or away from the body) as the cover layer and is centered about the product's longitudinal axis.

As indicated above, the absorbent layer 16 is preferably located about the central longitudinal axis of the product. The absorbent layer 16 may be formed of a material having parallel sides, or the absorbent layer material may have a varying width to correspond to an absorbent pad having a varying width along the length of the pad 10. The maximum absorbent layer width Z is less than the maximum pad width X. The absorbent layer 16 may extend to a narrow portion of the lateral sides 18 of the product. In a preferred embodiment, the absorbent layer 16 is spaced away from the lateral sides 18 along the length of the product. More preferably, the absorbent layer 16 is spaced from the lateral edges 18 by at least about 1 mm. More preferably, the absorbent layer 16 is spaced from the lateral edges 18 by at least about 2 mm, and most preferably, by at least about 4 mm.

The pad 10 has a barrier layer 14 which is located adjacent to the absorbent layer 16 in the central longitudinal portion of the product and to the cover layer 12 in portions elsewhere. The barrier layer 14 prevents the absorbed fluid from staining a user's undergarment and may comprise any material which prevents or retards the passage of fluids. A representative, non-limiting list of barrier layer materials includes liquid-impermeable films, microporous or discontinuous films, and gas-permeable/liquid-impermeable fabrics such as nonwoven, woven and knitted fabrics. A preferred barrier 14 is a 0.8 mil, polypropylene film, supplied by the Edison Plastics Co. (Newport News, Va.) as code XP-766-B.

Preferably, the layers 12, 14, 16 of the pad 10 may be attached to one another to form a cohesive unit to enhance the pad's stability. The attachment may be by any known means, including adhesive, ultrasonics, co-embossing, thermobonding, mechanical bonding, and the like. In its preferred embodiment, the pad 10 has construction adhesive 26 present between the cover layer 12 and the absorbent layer 16 and also present between the absorbent layer 16 and the barrier layer 14. The construction adhesive 26 serves to hold the layers 12, 14, 16 together and to minimize pad deformation during use. Preferably, the construction adhesive 26 is a hot melt adhesive supplied by the H.B. Fuller Company (St. Paul, Minn.) as code HL 1308x. The adhesive can be applied as either a thin porous film, or in a random spray, in a controlled spiral pattern, or in any other application pattern. The adhesive coat weight is approximately 10 mg./in$^2$.

In laminated products, the peripheral edges 18, 20 are often subjected to forces which may delaminate the product if these edges do not have sufficient "z-directional" strength. If the laminated product lies in an "x-y plane", the z-direction relates to the thickness of the product. Therefore, the peripheral edges 18, 20 of the product should have sufficient z-directional strength to resist the anticipated delamination forces normally encountered by the product. Preferably, the z-directional strength of the end of the product is about 0.75 to about 2 lbs/inch width, and the z-directional strength of the side of the product is about 0.4 to about 1.2 lbs/inch width. This z-directional strength can be achieved by incorporating thermoplastic material in the peripheral seal. Thermoplastic materials may be found in the cover layer, the absorbent layer, the barrier layer, and between two or more of these layers. The materials can be integral portions of these layers such as fibers and films or they can be added such as additional adhesives, foams, particulate materials such as powders and encapsulated materials, emulsions, and the like.

The z-directional strength can be measured using a stress/strain apparatus (such as Instron Tensile Tester Model 1130, 1122, 4201, 4301 or equivalent with charting capability), a load cell (measuring less than 25 lbs), pneumatic jaw grips (one to two inches), and a precision one inch paper cutter as follows:

The Tensile Tester should be set to a crosshead speed of 12 in/min., a gauge length of 0.75 in., with a full scale load of less than or equal to 5 lbs. One inch wide samples are cut along the length or width direction of a product, and these samples are cut in half to provide a test sample of anterior and posterior longitudinal ends and left and right transverse side samples. Identify these samples for recording. Separate the barrier film and any adhered bottom veneer from the absorbent layer to ⅛ in. from any perimeter seal. If no perimeter seal, separate enough barrier film to allow the sample to be clamped in the Tester jaws. Place the barrier film in the moving jaw and the absorbent core/cover in the fixed jaw. Begin the crosshead, chart the loads measured, and record the peak load for all samples.

The z-directional strength may be achieved by sealing along the perimeter 18, 20 of the product, or the laminate layers 12, 14, 16 may have sufficient internal and inter-layer strength throughout the product that additional sealing along the perimeter 18, 20 is unnecessary. If the laminate requires sealing along the perimeter, it is preferred that the sealing mechanism selected is compatible with the material used to form the individual laminate layers.

The perimeter seal 24 may be formed by any method of attaching layers together, including without limitation, ultrasonics, adhesives, thermobonding, embossing, or any combination of these. In the preferred embodiment of the present invention, the perimeter seal 24 is formed by crimping involving the application of heat and pressure to bond the layers together. Thus, in this preferred embodiment, the body-side cover 12, the absorbent layer 16, and the barrier layer 14 preferably include a sufficient amount of a thermoplastic material to flow during the sealing process. This thermoplastic material may be found in one or more of the body-side cover layer 12, the absorbent layer 16, the barrier layer 14, thermoplastic adhesive 26 between these layers.

The resulting perimeter seal 24 has sufficient z-directional strength to resist delamination. Preferably, the perimeter seal 24 at the ends 20 of the pad 10 captures the absorbent layer 16, the cover 12, and the barrier 14, and the perimeter seal 24 along the sides 18 of the pad 10 captures only the cover 12 and the barrier 14. Therefore, the perimeter seal 24 along the pad's sides 18 is less stiff than the perimeter seal 24 at the pad's ends 20. This stiffness may be measured using a Twing Albert PCA Score Bend Tester (available from Twing Albert Instrument Co., Philadelphia, Pa.) used in the following manner:

One inch wide samples are cut along the length or width direction of a product. Identify these samples for recording. Calibrate the Tester, set the selector switch to bending force, set the toggle switch to 90° reverse position, attach stirrup to pins under upper "v" block, and position digital meter head and attach tilting plate string to stirrup, leaving slack. Prepare the test specimen by removing release paper and disabling any adhesive, e.g. with talc, if necessary. Place test specimen into Tester, centered on the tilting plate, and close the clamping plate. Record the maximum digital force reading and record.

Generally, the ratio of stiffness of ends 20 of the products to the sides 18 is about 1.1:1. Preferably, the ratio is about 1.1:1 to 100:1, more preferably about 1.5:1 TO 3:1. Other ratios may be useful including 1.1:1 to 10:1. These ratios can result from stiffness measurements of the longitudinal ends 20 of about 30 to about 55 g/inch width, and of the lateral sides 18 of about 15 to about 25 g/inch width.

The preferred pad has an attachment means 28 to maintain it in a desired location during use. Preferably, the attachment means 28 is disposed on the garment facing side of the barrier layer 14. However, it will also be recognized that the attachment means 28 could be located on the body-facing side 12, at the edges 18, and at combinations of these locations. Preferably, the attachment means 28 attaches the pad 10 to the user's undergarment and keeps the pad properly positioned during use.

Suitable attachment means 28 are known in the art and include pressure sensitive adhesives, cohesive-adhesives, frictional coatings, straps, belts, snaps, side flaps, and the like. A preferred attachment means is a pressure sensitive adhesive supplied by the H.B. Fuller Company (St. Paul, Minn.) as code HM 1972 or HM 3052. Preferably, the adhesive is applied as a thin film and covers the entire back of the product, except for zones 30 at the ends and corners of the product. These zones 30 are referred to as finger-lift areas and allow the user to easily remove the protective release liner 32 from the product prior to use. Of course one or more of these finger-lift areas may be deleted, e.g., allowing the adhesive to extend to the longitudinal ends 20. The adhesive coat weight is approximately 10 mg/in$^2$.

The pad 10 of the preferred embodiment has a release liner 32 which is adjacent to the positioning adhesive means 28. The release liner 32 serves to protect the positioning adhesive 28 from contamination prior to use. A preferred release liner 32 is a silicone coated paper which is supplied by the Akrosil Corp. (Menasha, Wis.) as code BL 25 MGA SILOX C3R/O or BL 40 MGA SILOX C4R/O.

Figure 4:
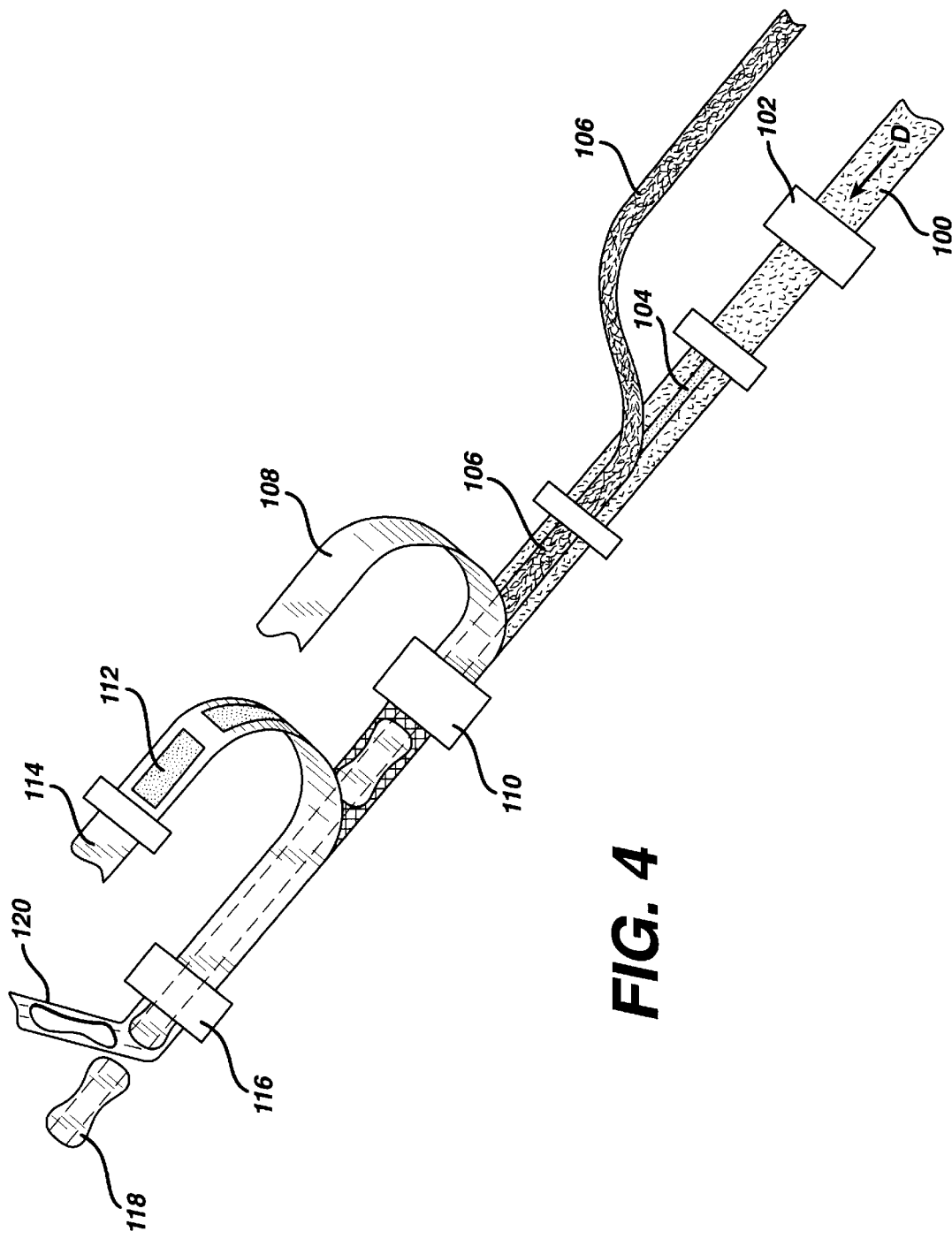
FIG. 4 is a schematic diagram of the manufacturing process of the present invention.

The component parts of the pad are assembled according to the schematic diagram illustrated in FIG. 4. The layers are oriented so that the body-facing surface of the body-side cover is facing downward.

The process begins by providing a continuous length of cover layer web 100 in a direction "D". The cover layer web 100 may be embossed with a floral or other decorative pattern at embossing station 102. Construction adhesive 104 may be applied continuously to the central portion of the web. A continuous length of absorbent layer web 106, which is narrower than the cover layer web 100, is placed directly on top of the central, adhesive-coated portion of the cover layer web 100. A second application of construction adhesive 104 may then take place across the full width of the combined cover/absorbent web. The barrier layer 108 is then placed on top of the combined cover/absorbent web. This cover/absorbent/barrier assembly is passed through a sealing station 110, where a sealing tool forms the perimeter seal. Preferably, the continuous absorbent layer 106, which is sandwiched between the cover layer web 100 and barrier 108, is aligned so that it is not captured by the perimeter seal at the pad sides.

Although the process has been described with construction adhesive 104 between the component layers 100, 106, 108, it is important to note that the layers need not be joined together at all, except in the perimeter seal, or that the layers may be joined together by means other than adhesive as mentioned above. In addition, if the laminate layers have sufficient internal z-directional strength, and the inter-layer attachment is sufficiently strong, the additional perimeter seal may be eliminated.

Positioning adhesive 112 is applied to the silicone coated side of the release liner 114. The release liner/positioning adhesive web is then combined with the cover/absorbent/barrier web so that the positioning adhesive 112 comes into direct contact with the garment facing side of the barrier web 108. The combined web is then fed into a rotary cutting station 116 to cut out individual finished products 118. Thereafter, the excess trim material 120 is removed and the final pad 118 is sent for packaging.

While the process described herein is a single lane process, the basic process steps can also be applied to a multiple (i.e. 2 or more) lane process in order to reduce the trim waste associated with each product and to increase machine throughput.

EXAMPLES

The present invention will be further understood by reference to the following specific Examples which are illustrative of the composition, form and method of producing the multilayered panty liner product of the present invention. It is to be understood that many variations of composition, form and method of producing the panty liner product would be apparent to those skilled in the art. The following Examples, wherein parts and percentages are by weight unless otherwise indicated, are only illustrative.

Pantiliners were manufactured in a dual lane apparatus according to the following general process: An open adhesive pattern was applied to two central portions spaced about 2.4 inches apart (center-to-center) of a continuous length of an absorbent cover layer having a width of about 5.5 inches. Two continuous lengths of absorbent layer web, each having a width of about 1.5 inches, were placed directly on top of each respective central, adhesive-coated portion of the cover layer. Additional adhesive was then applied in an open pattern across the full width of the combined cover/absorbent web. The barrier layer was placed on top of the combined cover/absorbent web. This cover/absorbent/barrier assembly was passed through a sealing station, where a sealing tool formed the perimeter seal by the application of heat and pressure. The continuous absorbent layer was aligned along the center line of each pad so that it was not captured by the perimeter seal at the pad sides.

Positioning adhesive was applied to the silicone coated side of a release liner. The release liner/positioning adhesive web was then adhered to the garment-facing side of the barrier. The combined web was then fed into a cutting station to cut out individual finished products. The finished products had the shape illustrated in FIG. 1 with a cover surface area of about 13.25 in$^2$, and an absorbent layer surface area of about 9.2 in$^2$. This process was modified by using different cover and absorbent layers as described below:

TABLE 1

| Example | Cover Layer | Absorbent Layer |
| --- | --- | --- |
| 1 | Chicopee 4086 | Chicopee 4086 |
| 2 | Chicopee 4086 | Merfin 9125TX258 |
| 3 | Merfin 907002DX238 | Chicopee 4086 |
| 4 | Merfin 907002DX238 | Merfin 9115T |

Chicopee 4086 is a nonwoven fabric having a basis weight of 85 g/m$^2$ which is a blend of 46 wt-% bicomponent fibers (polyester core, polyethylene sheath) and 54 wt-% pulp. It is available from Chicopee, Inc., North Little Rock, Ark., USA.

Merfin 9125TX258 is a nonwoven fabric having a basis weight of 125 g/m$^2$ which is a blend of 20 wt-% bicomponent fibers (polyester core, polyethylene sheath), 30 wt-% superabsorbent powder, and 50 wt-% pulp. It is available from Merfin Hygienic Products, Ltd., Delta, British Columbia, Canada.

Merfin 907002DX238 is a nonwoven fabric having a basis weight of 70 g/m$^2$ which is a blend of 2 wt-% binder, 20 wt-% bicomponent fibers (polyester core, polyethylene sheath), and 78 wt-% pulp. It is available from Merfin Hygienic Products, Ltd.

Merfin 9115T is a nonwoven fabric having a basis weight of 115 g/m$^2$ which is a blend of 2 wt-% binder, 20 wt-% bicomponent fibers (polyester core, polyethylene sheath), 68 wt-% pulp, and 10 wt-% calcium carbonate. It is available from Merfin Hygienic Products, Ltd.

These products were measured to determine the force necessary to bend the perimeter seal area 90°, both at the longitudinal ends where this seal includes the absorbent layer and at their lateral sides where the seal does not include this layer. The z-directional strength of their perimeter seals was also measured, both dry and after having been saturated by distilled water. The results of these measurements are included in Table 2 below. Each reported value reflects the mean of eight measurements.

TABLE 2

| Example | Bending Force Dry (g/in) | Std. Dev. | Z-dir. Dry (lb/in) | Std. Dev. | Z-dir. Wet (lb/in) | Std. Dev. |
| --- | --- | --- | --- | --- | --- | --- |
| 1 End | 43 | 6 | 0.98 | 0.31 | 0.71 | 0.21 |
| 1 Side | 21 | 4 | 0.96 | 0.17 | 0.88 | 0.18 |
| 2 End | 42 | 3 | 0.94 | 0.15 | 0.73 | 0.10 |
| 2 Side | 19 | 2 | 0.86 | 0.17 | 0.84 | 0.14 |
| 3 End | 42 | 6 | 1.46 | 0.45 | 1.28 | 0.33 |
| 3 Side | 21 | 3 | 0.60 | 0.07 | 0.43 | 0.08 |
| 4 End | 38 | 3 | 0.85 | 0.10 | 0.74 | 0.11 |
| 4 Side | 21 | 3 | 0.46 | 0.06 | 0.31 | 0.02 |

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of making a sanitary napkin comprising the steps of: providing a continuous length of a cover layer having a first width; providing a continuous length of an absorbent layer having a second width, less than the first width;

superposing the absorbent layer on one surface of the cover layer, spaced inward from one side edge of the cover layer; laminating the absorbent layer to the cover layer to form an absorbent laminate;

laminating a barrier layer to the absorbent laminate to form a laminated web, wherein the absorbent layer is positioned between the cover layer and the barrier layer and the barrier layer has a width substantially corresponding to the first width; and cutting the laminated web; thereby forming a sanitary napkin having a perimeter with lateral sides and longitudinal ends; wherein the ratio of the bending force of the longitudinal ends to the lateral sides is about 1.1:1 to about 100:1.

2. The method of claim 1 wherein the step of laminating the absorbent layer to the cover further comprises the step of applying a thermoplastic adhesive between the absorbent layer and the cover layer.

3. The method of claim 1 wherein the step of laminating the barrier layer to the absorbent laminate further comprises the step of applying a thermoplastic adhesive between the barrier layer and the absorbent laminate.

4. The method of claim 1 which further comprises the step of sealing the perimeter of the sanitary napkin.

5. The method of claim 4 wherein the step of sealing the perimeter comprises applying heat and pressure.

6. The method of claim 5 wherein thermoplastic material flows to integrate with non-thermoplastic material.

7. The method of claim 1 wherein the absorbent layer is spaced a distance from the perimeter along lateral sides of the absorbent article.

8. The method of claim 1 wherein a plurality of absorbent webs are superposed on one surface of the cover layer, each absorbent web being spaced inward from one side edge of the cover layer.

9. The method of claim 8 wherein each absorbent web defines a processing lane in a multi-lane process.

10. The method of claim 1 wherein the ratio of bending force of longitudinal ends to lateral sides is about 1.5:1 to about 3:1.

11. The method of claim 1 wherein the bending force of the longitudinal ends is about 30 to about 55 g/in. width, and the bending force of the lateral sides is about 15 to about 25 g/in. width.

* * * * *